(12) United States Patent
Urmanov et al.

(10) Patent No.: US 7,475,047 B1
(45) Date of Patent: Jan. 6, 2009

(54) PARALLEL GROUPING DECOMPOSITION FOR FAST TRAINING OF LARGE-SCALE SUPPORT VECTOR MACHINES

(75) Inventors: Aleksey M. Urmanov, San Diego, CA (US); Anton A. Bougaev, Lafayette, IN (US); Kenny C. Gross, San Diego, CA (US)

(73) Assignee: Sun Microsystems, Inc., Santa Clara, CA (US)

( * ) Notice: Subject to any disclaimer, the term of this patent is extended or adjusted under 35 U.S.C. 154(b) by 323 days.

(21) Appl. No.: 11/081,983

(22) Filed: Mar. 16, 2005

(51) Int. Cl.
*G06F 15/18* (2006.01)
(52) U.S. Cl. .......................... 706/12; 706/924
(58) Field of Classification Search .................. 706/16, 706/12, 20, 25, 45, 48, 46, 47, 21, 15, 924; 709/214, 201, 225
See application file for complete search history.

(56) References Cited

U.S. PATENT DOCUMENTS 6,427,141 B1 * 7/2002 Barnhill ........................ 706/16
2005/0052287 A1 * 3/2005 Milenova et al. ............. 707/102

OTHER PUBLICATIONS

'Mixture of SVMs for face class modeling': Meynet, MLMI 2004, LNCS 3361, pp. 173-181.*

'An Introduction to Support Vector Machines and other kernel based learning methods': Cristianini, 2000, Canbridge University Press, p. 79, 136-137.*
'A parallel mixture of SVM's for a very large scale problems': Collobert, 2002, MIT, neural computation 14, 1105-1114.*
'Rough sets method for SVM data preprocessing': Li, 2004, IEEE, 0-78038643-4, pp. 1039-1042.*
'Optimized support vector machines for nonstationary signal classification': Davy, 2002, IEEE, 10709908, IEEE signal processing letters, vol. 9, No. 12, pp. 442-445.*

* cited by examiner

*Primary Examiner*—Joseph P. Hirl
*Assistant Examiner*—Peter Coughlan
(74) *Attorney, Agent, or Firm*—Park, Vaughan & Fleming LLP; Shun Yao

(57) ABSTRACT

One embodiment of the present invention provides a system that performs parallel grouping decomposition to facilitate expedited training of a support vector machine (SVM). During operation, the system receives a training dataset comprised of data vectors. The system then determines whether any data vector in the dataset violates conditions associated with a current SVM. Next, the system divides the violating data vectors into a number of subsets, thereby allowing parallel SVM training for each subset. The system subsequently builds an independent SVM for each subset in parallel based on the current SVM. The system then constructs a new SVM to replace the current SVM based on the SVMs built for each subset of violating data vectors.

18 Claims, 4 Drawing Sheets

US 7,475,047 B1

PARALLEL GROUPING DECOMPOSITION FOR FAST TRAINING OF LARGE-SCALE SUPPORT VECTOR MACHINES

BACKGROUND

The present invention relates to techniques for computer-based classification, which can be used to identify members of groups of interest within datasets.

Classification and pattern recognition techniques have wide-reaching applications. For example, a number of life science applications use classification techniques to identify members of groups of interest within clinical datasets. In particular, one important application involves distinguishing the protein signatures of patients with certain type of cancer from the protein signatures of patients who do not. This problem stems from the need in clinical trials to test the efficacy of a drug in curing cancer while the cancer is at an early stage. In order to do so, one needs to be able to identify patients who have cancer at an early stage.

Conventional diagnostic techniques are not sufficient for this application. A popular technique (from an area that has become known as "proteomics") is to analyze mass spectra, which are produced by a mass spectrometer from serum samples of patients. Depending on the type of cancer, the mass spectra of serum samples can show distinct signatures, which are not immediately visible to the naked eye. Several existing data mining techniques are presently used to distinguish the cancer spectra from the normal ones, such as Naïve Bayes, Decision Trees, Principle-Components-Analysis based techniques, Neural Networks, etc.

However, these existing techniques are characterized by false-alarm and missed-alarm probabilities that are not sufficiently small. This is a problem because false alarms can cause patients to experience anxiety, and can cause them submit to unnecessary biopsies or other procedures, while missed alarms can result in progression of an undetected disease.

Support Vector Machines (SVMs) provide a new approach to pattern classification problems. SVM-based techniques are particularly attractive for the cancer classification problem because SVM-based techniques operate robustly for high-dimensional feature data, unlike other techniques which have resource requirements that are closely coupled with feature dimensions.

However, the application of SVM's in areas involving huge datasets, such as in proteomics, is constrained by extremely high computation cost, in terms of both the compute cycles needed as well as enormous physical memory requirements.

For example, a quadratic optimization problem arises during the training phase of the SVM's for large datasets, which are common in most life sciences problems. Such a quadratic optimization problem typically requires the memory to accommodate an N×N matrix, where N is the number of data vectors. This creates huge challenges for conventional high-end enterprise computer servers when the input datasets contain thousands or tens of thousands of data vectors. In addition, the training time for the algorithm grows in a manner that is polynomial in N. Current state-of-the-art research papers propose using heuristic, data-level decomposition approaches; but often these heuristic approaches are designed with little or no quantitative justification and suboptimal results.

SUMMARY

One embodiment of the present invention provides a system that performs parallel grouping decomposition to facilitate expedited training of a support vector machine (SVM). During operation, the system receives a training dataset comprised of data vectors. The system then determines whether any data vector in the dataset violates conditions associated with a current SVM. Next, the system divides the violating data vectors into a number of subsets, thereby allowing parallel SVM training for each subset. The system subsequently builds an independent SVM for each subset in parallel based on the current SVM. The system then constructs a new SVM to replace the current SVM based on the SVMs built for each subset of violating data vectors.

In a variation of this embodiment, if any data vector in the dataset violates conditions associated with the new SVM, the system iteratively performs the following operations until no data vector violates conditions associated with the SVM. The system first determines whether any data vector violates conditions associated with the current SVM. The system then divides the violating data vectors into subsets. Next, the system builds an independent SVM for each subset in parallel based on the current SVM. The system subsequently constructs a new SVM to replace the current SVM based on the SVMs built for each subset.

In a variation of this embodiment, the initial SVM contains either no support vectors, or a set of existing support vectors obtained based on prior knowledge of the dataset.

In a variation of this embodiment, building the independent SVM for each subset involves adding the support vectors for the current SVM to the subset, so that each subset contains violating data vectors and all the support vectors for the current SVM.

In a variation of this embodiment, building the independent SVM for each subset in parallel involves solving quadratic optimization problems for each subset in parallel, thereby reducing the total processing time.

In a variation of this embodiment, constructing the new SVM involves collecting support vectors for each SVM built for the subsets, removing duplicates from the collected support vectors, and forming the new SVM based on the collected support vectors.

In a variation of this embodiment, determining whether any vector in the dataset violates conditions associated with the SVM involves evaluating whether each data vector violates a set of Karush-Kuhn-Tucker (KKT) conditions for the current SVM.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The data structure and code described in this detailed description are typically stored on a computer readable storage medium, which may be any device of medium that can store code and/or data for use by a computer system. This includes, but is not limited to, magnetic and optical storage devices, such as disk drives, magnetic tape, CDs (compact discs) and DVDs (digital versatile discs or digital video discs).

Multiprocessor System

Figure 1:
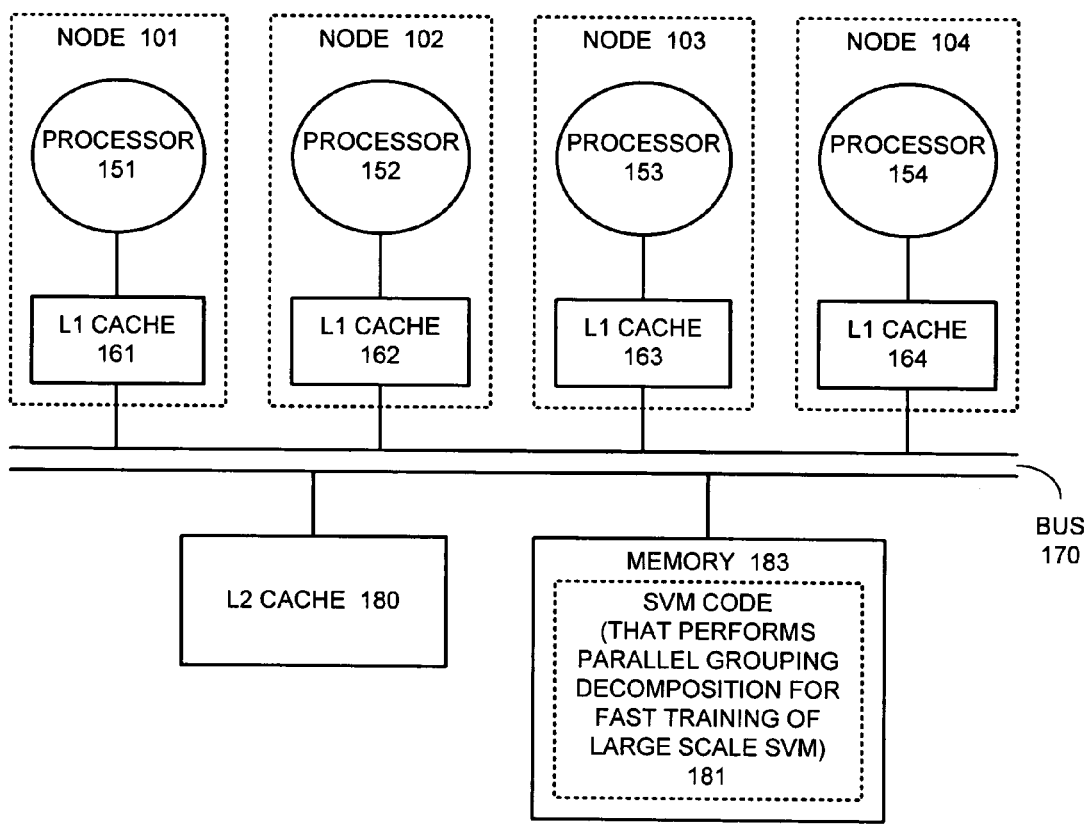
FIG. 1 illustrates a multiprocessor system in accordance with an embodiment of the present invention.

FIG. 1 illustrates an exemplary multiprocessor system 100 in accordance with an embodiment of the present invention. Multiprocessor system 100 is a shared-memory multiprocessor system, which includes a number of processors 151-154 coupled to level one (L1) caches 161-164 which share a level two (L2) cache 180 and a memory 183. Memory 183 contains SVM code that performs parallel grouping decomposition for fast training of large scale SVMs. This parallel grouping decomposition process is described in more detail below.

During operation, if a processor 151 accesses a data item that is not present in local L1 cache 161, the system attempts to retrieve the data item from L2 cache 180. If the data item is not present in L2 cache 180, the system first retrieves the data item from memory 183 into L2 cache 180, and then from L2 cache 180 into L1 cache 161.

Multiprocessor system 100 also supports a coherency protocol that operates across bus 170. This coherency protocol ensures that if one copy of a data item is modified in L1 cache 161, other copies of the same data item in L1 caches 162-164, in L2 cache 180 and in memory 183 are updated or invalidated to reflect the modification.

Although the present invention is described in the context of the shared-memory multiprocessor system 100, the present invention is not meant to be limited to such a system. In general, the present invention can operate in any computer system or distributed system which contains multiple processors. For example, the present invention can operate in a distributed computing system in which separate computing systems are coupled together through a network. Hence, the term "multiprocessor system," as used in this specification and the appended claims, refers to any computer system or distributed system containing multiple processors which can work together on a given computational task.

Support Vector Machine

One embodiment of the present invention provides unique advantages which enable training of large scale SVMs in reasonable time using limited resources and. This procedure reformulates the SVM training problem into a quadratic optimization problem (QP) with specific constraints on the variables. In this way, standard numerical solvers can be used to solve SVM training problems. The rest of this section explains the process of formulating an SVM training problem into a quadratic problem.

First, let $X_i$ denote an m-dimensional vector, i.e., $X_i \in R^m$. Vector $X_i$ represents a data point in a data set, such as a snapshot of the physical telemetry signals of a computer server or a protein mass spectrum obtained from a mass spectrometer. In addition, let D denote a data set of n such data points:

$D = \{X_i, Y_i\}$, $i = 1, \ldots, n$ where $Y_i \in \{-1, +1\}$ represents the presence (+1) or absence (−1) of the property or feature of interest for point $X_i$. Data set D is generally called a training data set, because it is used to build an SVM.

For example, $X_i$ can be a sample of a blood mass spectrum. Each element of a vector data point represents an amplitude at a certain m/z value. A nonzero amplitude means that there is a peptide or a peptide fragment with such mass in the blood sample. $Y_i$ represents the absence (−1) or presence (+1) of cancer in the patient. The goal is to build a classifier that uses X as an input and then correctly classifies the patient as having cancer or not having cancer.

To build an SVM for classification, the training data set D ideally includes examples from patients with and without cancer. Then, the classifier learns a differentiating feature in the data set which separates data points associated with cancer patients from those associated with non-cancer patients.

Given a training set D, an SVM is built by solving the following prime quadratic problem ($QP_0$):

($QP_0$): min $\|W\|^2$, subject to the following constraints:

$$\begin{cases} (\Phi(X_i) \cdot W) + b) \geq 1 - \xi_i & \text{for } Y_i = +1 \\ (\Phi(X_i) \cdot W) + b) \leq -1 + \xi_i & \text{for } Y_i = -1 \\ \xi_i \geq 0, \forall i \end{cases}$$

where $\Phi$ is a mapping function from $R^m$ space to some Euclidean space H called feature space:

$\Phi: R^m \rightarrow H$.

Wherein $W \in H$ is a vector normal to the hyperplane that separates the points representing the two classes, b is an unknown scalar, and $\xi_i$ is a set of positive slack variables representing the penalty of incorrect classification. The solution to the problem above defines an optimal separating hyperplane.

It is more convenient to solve a Lagrangian formulation of this problem:

$$(QP_1): \max \sum_i a_i - 0.5 \times \sum_{i,j} a_i a_j Y_i Y_j K(X_i, X_j),$$

subject to the following constraints:

$$\begin{cases} 0 \leq a_i \leq C, i = 1, \ldots, n \\ \sum_i a_i Y_i = 0 \end{cases}$$

where $a_i$ is a set of Lagrange multipliers corresponding to the inequality constraints in the prime problem $QP_0$. Constant C represents the amount of penalty for incorrect classification, and $K(\cdot, \cdot)$ is a kernel function. Examples of kernel functions include $K(x,y) = x \cdot y$, $K(x,y) = (x \cdot y + 1)^p$, $K(x,y) = \tan h(kx \cdot y - \delta)$.

The optimal solution of problem $QP_1$, denoted as $a_i^*$, ideally satisfies the following conditions, namely the Karush-Kuhn-Tucker (KKT) conditions, of the prime problem $QP_0$:

$$\begin{cases} Y_i\left(\sum_j a_j Y_j K(X_i, X_j) + b\right) - 1 \geq 0; \text{ for } a_i = 0 \\ Y_i\left(\sum_j a_j Y_j K(X_i, X_j) + b\right) - 1 = 0; \text{ for } 0 < a_i < C \\ Y_i\left(\sum_j a_j Y_j K(X_i, X_j) + b\right) - 1 \geq \xi_i; \text{ for } a_i = C, \xi_i \text{ is a positive scalar} \end{cases}$$

Data points $X_i$ for which there is a corresponding $0 < a_i < C$ are called support vectors and are denoted as $^S X_i$. Only support vectors are used for computing the separating hyperplane or for making a classification decision. All other data points can be removed from the training data set with no impact on the classification results.

The dimension of $QP_1$ is n, which is the number of data points in the training set. When n is large (e.g., n=1,000 or more), the classical sequential QP solvers become very slow and sometimes cannot find a solution at all. To overcome this problem, one embodiment of the present invention provides an approach for parallel processing of the quadratic problem $QP_1$, the solution of which produces the desired SVM.

Parallel Grouping Decomposition

One embodiment of the present invention uses a new technique called parallel grouping decomposition to perform SVM training in parallel. This approach allows solving arbitrarily large SVM problems using parallel processing. During operation, the system iteratively performs parallel grouping decomposition until a correct SVM is obtained. At the beginning of an iteration, the system first forms an initial support vector pool, $S = \{^S X_i, ^S Y_i, i=1, \ldots, ^S n\}$, based on prior knowledge about the problem, or based on the results from previous training procedures. (For example, the initial pool can be an empty set for a new problem.) Note that this pool serves as a starting point for adjusting the SVM to incorporate new information. When the training process is complete, this pool ideally contains the correct support vectors for the problem and the system accordingly exits the iteration.

Next, the system checks the KKT conditions for the prime quadratic problem $QP_0$ to determine if the current support vector pool S is the solution for the problem. If the KKT conditions are satisfied for each $a_i$, then the original $QP_0$ has been solved and the current pool S contains the correct support vectors for the solution SVM. Otherwise, the system finds all $a_i$'s which violate the KKT conditions and forms a separate data set $^V D$ of violating vectors:

$$^V_D = \{^V X_i, ^V Y_i\}, i=1, \ldots, ^V N$$

where $^V N$ is the total number of violators.

Note that the check of KKT conditions ideally is performed for all data vectors, because some of the vectors that violate the KKT conditions during a previous iteration may not be violators during the current iteration. Similarly, some of the data vectors that do not violate the KKT conditions during a previous iteration may violate the KKT conditions during the current iteration.

The system then divides the data set $^V D$ into G groups (subsets) denoted as $^V D^g$, where $g=1, \ldots, G$. The system may do so randomly, so that there can be approximately equal proportions of positive and negative examples in each group. The number of groups, G, can be specified as an adjustable parameter. Alternatively, the size of each group can be specified and G is computed as $G = \lceil ^V N / \text{Group\_Size} \rceil$.

The system subsequently adds to each subset $^V D^g$ the current support vectors, so that each subset contains a portion of KKT-violating data vectors and all of the support vectors contained in S:

$^V D^g = \{^V X_i^g, ^V Y_i^g, ^S X_j, ^S Y_j\}$ $i=1, \ldots, ^V N^g, j=1, \ldots, ^S n$.

The system then builds G independent SVMs for each subset in parallel. The system may use any available quadratic solver to solve these smaller quadratic problems. Because these quadratic problems are independent, all the necessary computations can be performed in parallel very efficiently.

After obtaining G SVMs for the G subsets, the system collects the support vectors from each of these SVMs and forms a new support vector pool S using these support vectors. Furthermore, the system removes any duplicate support vectors from the support vector pool S. The system then goes back to the beginning of the iteration to determine whether the SVM based on the current S is the correct solution. If so, the system exits. Otherwise, the system repeats the parallel-grouping decomposition again.

Typically, the number of data vector that violate the KKT conditions decreases with each iteration, although this may not always be the case. For practical purposes, the number of violators drops significantly with each iteration and only a few iterations are required to reach the final solution of the original problem. In essence, the parallel grouping decomposition approach divides large data sets into smaller, manageable subsets and finds the exact solution of the original QP problem iteratively while processing all subsets in parallel.

Figure 2:
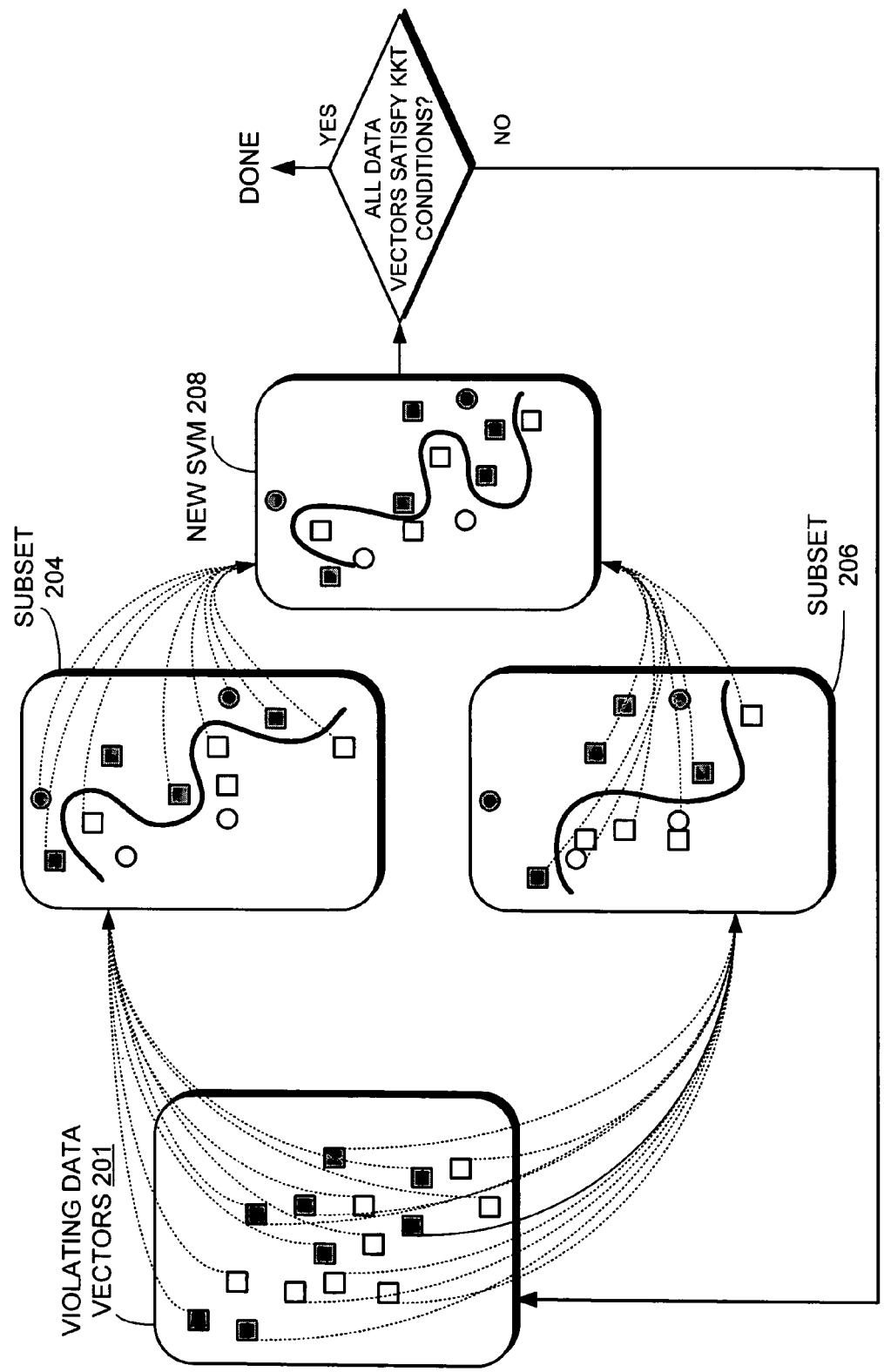
FIG. 2 illustrates the process of dividing violating data vectors into subsets in accordance with an embodiment of the present invention.

FIG. 2 illustrates the process of dividing violating data vectors into subsets in accordance with an embodiment of the present invention. In this example, a set of violating data vectors 201 is divided into two subsets, namely subset 204 and subset 206. Each subset contains approximately equal number of positive and negative examples (represented by grey squares and blank squares, respectively). The system then adds to each subset the current support vector pool. The current support vectors are represented in grey circles (positive examples) and blank circles (negative examples).

The system then builds an SVM for each subset, and collects the support vectors corresponding to each subset to form a new support vector pool. Next, the system builds a new SVM 208 based on the new support vectors. The system subsequently determines whether all the data vectors satisfy the KKT conditions for the problem. If so, the SVM training is complete and the system exits. Otherwise, the system repeats the parallel grouping decomposition process until it finds a correct SVM.

Figure 3:
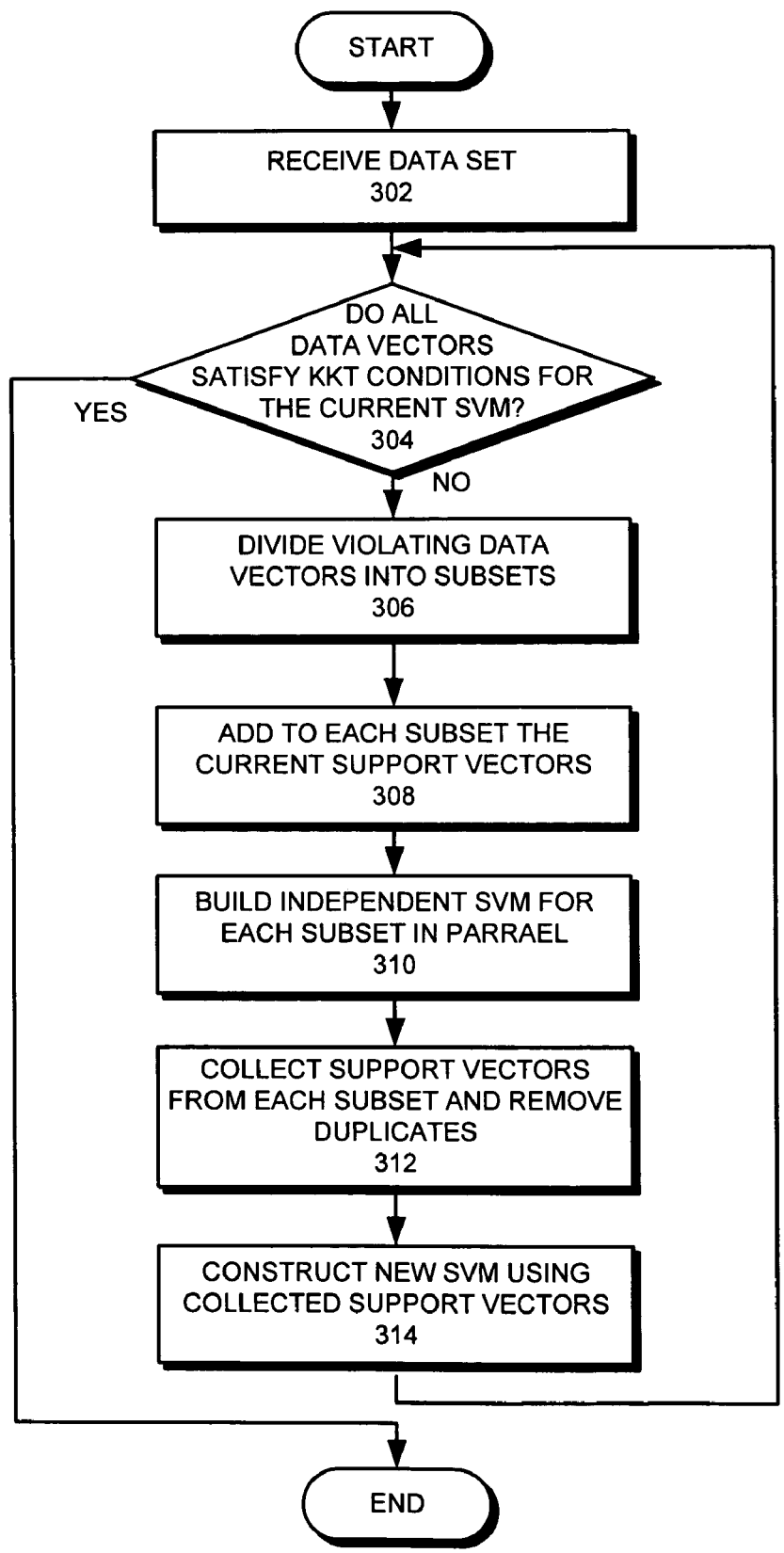
FIG. 3 illustrates presents a flow chart illustrating the process of parallel grouping decomposition in accordance with an embodiment of the present invention.

FIG. 3 illustrates presents a flow chart illustrating the process of parallel grouping decomposition in accordance with an embodiment of the present invention. During operation, the system starts by receiving a data set (step 302). The system then determines whether all data vectors satisfy KKT conditions for the current SVM (step 304). If so, the problem is solved and the system exits. Otherwise, the system divides the violating data vectors into a number of subsets (step 306). In addition, the system adds to each subset the current pool of support vectors (step 308).

Next, the system builds an independent SVM for each subset in parallel (step 310). After obtaining SVMs for the subsets, the system collects the support vectors from each subset and removes the duplicates (step 312). The system subsequently constructs a new SVM using the collected support vectors (step 314). The system then determines again whether all the data vectors satisfy the KKT conditions for the current SVM (step 304).

Figure 4:
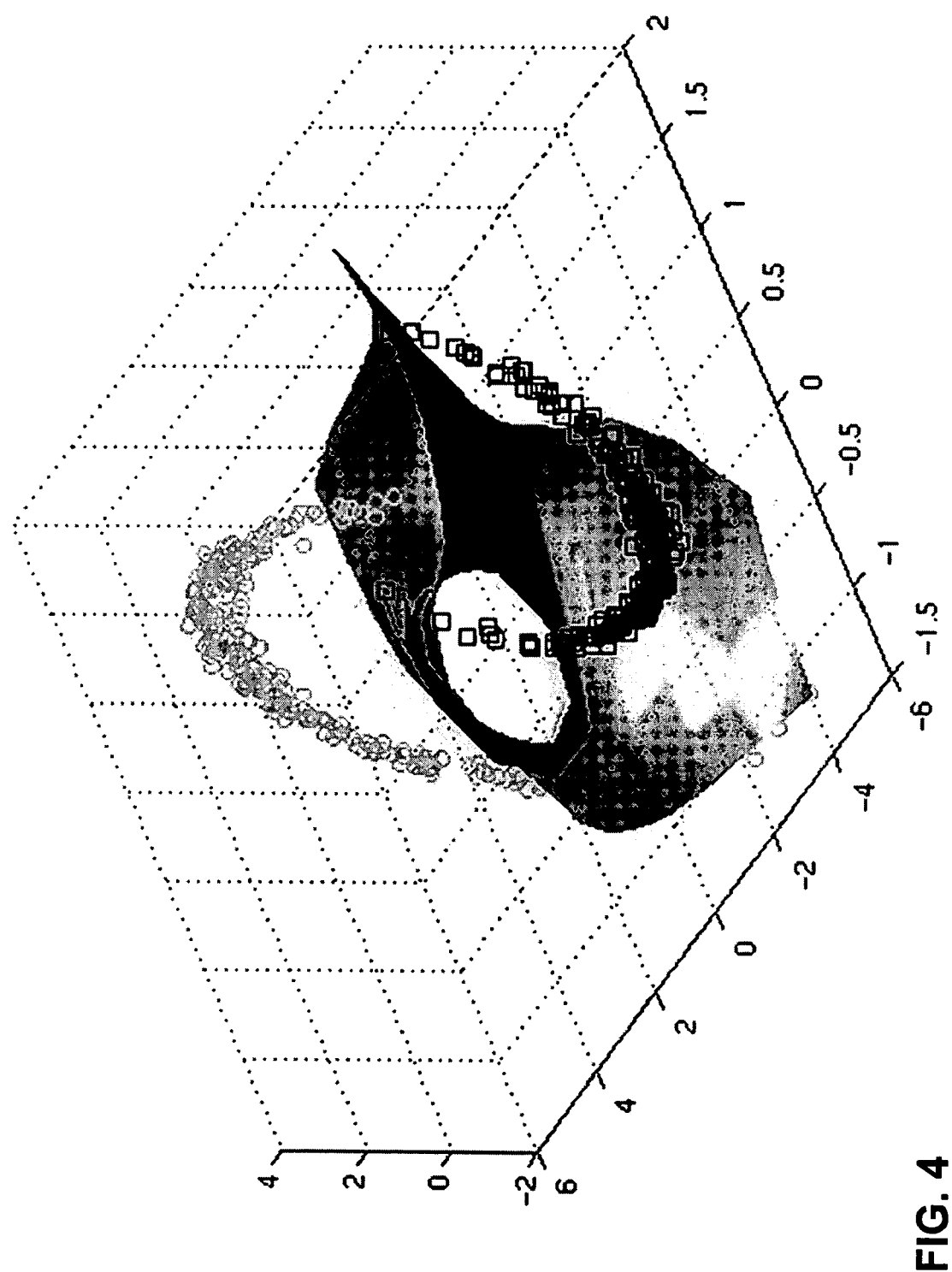
FIG. 4 illustrates a set of exemplary data vectors and a separating hyperplane in accordance with an embodiment of the present invention.

FIG. 4 illustrates a set of exemplary data vectors and a separating hyperplane in accordance with an embodiment of the present invention. In this example, the objective is to find an optimal separation of one set of observations (represented by dark squares) from another set of observations (represented by grey circles). As can be observed in FIG. 4, this is a challenging problem because there is a "double horseshoe" relationship between the two sets of observations. It is obvious that naïve approaches which produce a linear line or linear plane to separate these two classes will result in numerous misidentifications.

Using the present parallel grouping decomposition approach, a system can easily solve this problem. In one exemplary experiment, the original data set is partitioned into 24 groups during the first iteration. After the first iteration, only a few vectors violate the KKT conditions. Therefore, the second iteration includes only one grup of violators combined with the support vectors obtained during the first iteration. After the second iteration, all the data vectors satisfy the KKT conditions and the original problem is solved in a total of 0.13 time units. By contrast, the same problem is solved by a state-of-art conventional SVM training system in a total of 0.51 time units.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A computer implemented method for performing parallel grouping decomposition to facilitate expedited training of a support vector machine (SVM), comprising:
    receiving a training dataset comprised of data vectors;
    determining whether any data vector in the dataset violates a set of Karush-Kuhn-Tucker (KKT) conditions associated with a current SVM;
    dividing the violating data vectors into a number of subsets containing approximately equal proportions of positive and negative examples in each subset, wherein the number of groups can be specified as an adjustable parameter, thereby allowing parallel SVM training for each subset;
    adding to each subset support vectors associated with the current SVM, wherein the support vectors are those data vectors in the dataset for which there is a corresponding number between zero and a constant, wherein the constant represents an amount of penalty for an incorrect classification and the corresponding number is a Lagrange multiplier corresponding to an inequality constraint in a prime problem;
    building at least one independent SVM for each subset in parallel;
    constructing a new SVM to replace the current SVM by forming a set that contains support vectors from each of the independent SVMs;
    receiving test data comprised of one or more observations of one or more physical characteristics of a physical object under test; and
    producing a result to indicate a physical state the object under test is in, based on the test data and the SVM.

2. The method of claim 1, wherein if any data vector in the dataset violates the set of KKT conditions associated with the new SVM, the method further comprises iteratively performing the following operations until no data vector violates conditions associated with the SVM:
    determining whether any data vector violates the set of KKT conditions associated with the current SVM;
    dividing the violating data vectors into subsets containing approximately equal proportions of positive and negative examples in each subset, wherein the number of groups can be specified as an adjustable parameter;
    building an independent SVM for each subset in parallel based on the current SVM; and
    constructing a new SVM to replace the current SVM by adding the support vectors for the current SVM to the subset, so that each subset contains violating data vectors and all the support vectors for the SVMs built for each subset.

3. The method of claim 1, wherein the initial SVM contains either no support vectors, or a set of existing support vectors obtained based on prior knowledge of the dataset.

4. The method of claim 1, wherein building the independent SVM for each subset involves adding the support vectors for the current SVM to the subset, so that each subset contains violating data vectors and all the support vectors for the current SVM.

5. The method of claim 1, wherein building the independent SVM for each subset in parallel involves solving quadratic optimization problems for each subset in parallel, thereby reducing the total processing time.

6. The method of claim 1, wherein constructing the new SVM involves:
    collecting support vectors for each SVM built for the subsets;
    removing duplicates from the collected support vectors; and
    forming the new SVM by adding the set of support vectors for the current SVM to the subset, so that each subset contains violating data vectors and the collected support vectors with the duplicates removed.

7. A computer-readable storage medium storing instructions that when executed by a computer cause the computer to perform a method for performing parallel grouping decomposition to facilitate expedited training of a support vector machine (SVM), comprising:
    receiving a training dataset comprised of data vectors;
    determining whether any data vector in the dataset violates a set of Karush-Kuhn-Tucker (KKT) conditions associated with a current SVM;
    dividing the violating data vectors into a number of subsets containing approximately equal proportions of positive and negative examples in each subset, wherein the number of groups can be specified as an adjustable parameter, thereby allowing parallel SVM training for each subset;
    adding to each subset support vectors associated with the current SVM, wherein the support vectors are those data vectors in the dataset for which there is a corresponding number between zero and a constant, wherein the constant represents an amount of penalty for an incorrect classification and the corresponding number is a Lagrange multiplier corresponding to an inequality constraint in a prime problem;
    building at least one independent SVM for each subset in parallel;
    constructing a new SVM to replace the current SVM by forming a set that contains support vectors from each of the independent SVMs;
    receiving test data comprised of one or more observations of one or more physical characteristics of a physical object under test; and producing a result to indicate a physical state the object under test is in, based on the test data and the new SVM.

8. The computer-readable storage medium of claim 7, wherein if any data vector in the dataset violates the set of KKT conditions associated with the new SVM, the method further comprises iteratively performing the following operations until no data vector violates conditions associated with the SVM:
- determining whether any data vector violates conditions associated with the current SVM;
- dividing the violating data vectors into subsets containing approximately equal proportions of positive and negative examples in each subset, wherein the number of groups can be specified as an adjustable parameter;
- building an independent SVM for each subset in parallel based on the current SVM; and
- constructing a new SVM to replace the current SVM by adding the support vectors for the current SVM to the subset, so that each subset contains violating data vectors and all the support vectors for the SVMs built for each subset.

9. The computer-readable storage medium of claim 7, wherein the initial SVM contains either no support vectors, or a set of existing support vectors obtained based on prior knowledge of the dataset.

10. The computer-readable storage medium of claim 7, wherein building the independent SVM for each subset involves adding the support vectors for the current SVM to the subset, so that each subset contains violating data vectors and all the support vectors for the current SVM.

11. The computer-readable storage medium of claim 7, wherein building the independent SVM for each subset in parallel involves solving quadratic optimization problems for each subset in parallel, thereby reducing the total processing time.

12. The computer-readable storage medium of claim 7, wherein constructing the new SVM involves:
- collecting support vectors for each SVM built for the subsets;
- removing duplicates from the collected support vectors; and
- forming the new SVM by adding the set of support vectors for the current SVM to the subset, so that each subset contains violating data vectors and the collected support vectors with the duplicates removed.

13. An apparatus for performing parallel grouping decomposition to facilitate expedited training of a support vector machine (SVM), comprising:
- a processor which: a receiving mechanism configured to receive a training dataset comprised of data vectors;
- a decision mechanism configured to determine whether any data vector in the dataset violates a set of Karush-Kuhn-Tucker (KKT) conditions associated with a current SVM;
- a grouping mechanism configured to divide the violating data vectors into a number of subsets, thereby allowing parallel SVM training for each subset;
- a addition mechanism configured to divide the violating data vectors into a number of subsets, thereby allowing parallel SVM training for each subset; wherein the support vectors are those data vectors in the dataset for which there is a corresponding number between zero and a constant, wherein the constant represents an amount of penalty for an incorrect classification and the corresponding number is a Lagrange multiplier corresponding to an inequality constraint in a prime problem;
- a number of quadratic optimizations configured to build at least one independent SVM for each subset in parallel based on the current SVM;
- a construction mechanism configured to construct a new SVM to replace the current SVM by forming a set that contains support vectors from each of the independent SVMs; receiving test data comprised of one or more observations of one or more physical characteristics of a physical object under test; and producing a result to indicate a physical state the object under test is in, based on the test data and the new SVM.

14. The apparatus of claim 13, wherein if any data vector in the dataset violates conditions associated with the new SVM, the decision mechanism, the grouping mechanism, the quadratic optimizations, and the construction mechanism are configured to respectively perform the following operations iteratively until no data vector violates conditions associated with the SVM:
- determining whether any data vector violates the set of KKT conditions associated with the current SVM;
- dividing the violating data vectors into subsets containing approximately equal proportions of positive and negative examples in each subset, wherein the number of groups can be specified as an adjustable parameter;
- building an independent SVM for each subset in parallel based on the current SVM; and
- constructing a new SVM to replace the current SVM by adding the support vectors for the current SVM to the subset, so that each subset contains violating data vectors and all the support vectors for the SVMs built for each subset.

15. The apparatus of claim 13, wherein the initial SVM contains either no support vectors, or a set of existing support vectors obtained based on prior knowledge of the dataset.

16. The apparatus of claim 13, wherein while building the independent SVM for each subset, the quadratic optimizations are configured to add the support vectors for the current SVM to each subset, so that each subset contains violating data vectors and all the support vectors for the current SVM.

17. The apparatus of claim 13, wherein while building the independent SVM for each subset in parallel, the quadratic optimizations are configured to solve quadratic optimization problems for each subset in parallel, thereby reducing the total processing time.

18. The apparatus of claim 13, wherein while constructing the new SVM, the construction mechanism is configured to:
- collect support vectors for each SVM associated with the subsets;
- remove duplicates from the collected support vectors; and
- to form the new SVM by adding the set of support vectors for the current SVM to the subset, so that each subset contains violating data vectors and the collected support vectors with the duplicates removed.

* * * * *